(12) United States Patent
David et al.

(10) Patent No.: US 6,176,326 B1
(45) Date of Patent: Jan. 23, 2001

(54) SOIL SAMPLING MEASURING DEVICE

(75) Inventors: Ramon R. David, Holland; Saeid Yazdani, Byron Center, both of MI (US)

(73) Assignee: SoilCore, Inc., Holland, MI (US)

( * ) Notice: Under 35 U.S.C. 154(b), the term of this patent shall be extended for 0 days.

(21) Appl. No.: 09/167,168

(22) Filed: Oct. 6, 1998

(51) Int. Cl.$^7$ .............. E21B 49/00; G01N 1/00; G01N 1/04
(52) U.S. Cl. ............ 175/58; 175/20; 73/864.44
(58) Field of Search ............... 73/864.44, 864.45; 175/20, 58, 403; 172/22

(56) References Cited

U.S. PATENT DOCUMENTS

| | | |
|---|---|---|
| 1,737,718 | 12/1929 | Hausmann . |
| 1,847,136 | 3/1932 | Rauberstrauch . |
| 2,288,210 | 6/1942 | Schlumberger .................. 255/1 |
| 2,664,269 | 12/1953 | Knight et al. ................... 255/1 |
| 3,326,049 | 6/1967 | Eley ................................ 73/429 |
| 3,412,814 | 11/1968 | Rosfelder ........................ 175/6 |
| 3,497,018 | 2/1970 | Shultz et al. ................... 175/6 |
| 4,549,612 | 10/1985 | Cushing ......................... 175/20 |
| 4,729,437 | 3/1988 | Zapico ........................... 175/20 |
| 4,819,735 | 4/1989 | Puckett .......................... 172/22 |
| 4,989,678 | 2/1991 | Thompson ..................... 175/20 |
| 5,245,878 | 9/1993 | Underwood ................ 73/864.44 |
| 5,343,771 | 9/1994 | Turriff et al. ............... 73/864.44 |
| 5,505,098 | 4/1996 | Turriff et al. ............... 73/864.44 |
| 5,517,868 | 5/1996 | Turriff et al. ............... 73/864.44 |
| 5,522,271 | 6/1996 | Turriff et al. ............... 73/864.44 |
| 5,706,904 | 1/1998 | Turriff et al. .................. 175/28 |

*Primary Examiner*—Brian L. Johnson
*Assistant Examiner*—Joselynn Z. Sliteris
(74) *Attorney, Agent, or Firm*—Van Dyke, Gardner, Linn & Burkhart, LLP

(57) ABSTRACT

A soil sampling measuring device for collecting and measuring samples of soil for testing the volatile organic compounds in the soil. The soil sampling device includes a tactile indication of the volume of soil collected in the sampling device so that a person using the soil sampling device can determine when a desired volume of soil is collected in the soil sampling device without the need to refer to a visual scale. The soil sampling device includes a barrel and a plunger in the barrel, with at least one of the plunger and the barrel adapted to provide a change of resistance between the plunger and the barrel when the plunger is extended or retracted through the barrel which provides a tactile indication to the user of the soil sampling device that the plunger has reached a desired volume within the barrel. For example, the barrel of the device may include a rib or groove which respectively increases or decreases the friction between the plunger and the inner surface of the barrel. In preferred form, the plunger includes a shaft with a piston on one end and a handle on an opposed end from the piston and extends through one end of the barrel such that the piston frictionally engages the inner surface of the barrel. Alternately, the shaft of the piston may include either a rib or a groove which increases the resistance or decreases the resistance, respectively, between the shaft of the piston and the end wall of the barrel to provide a tactile indication of the position of the piston within the barrel.

17 Claims, 3 Drawing Sheets

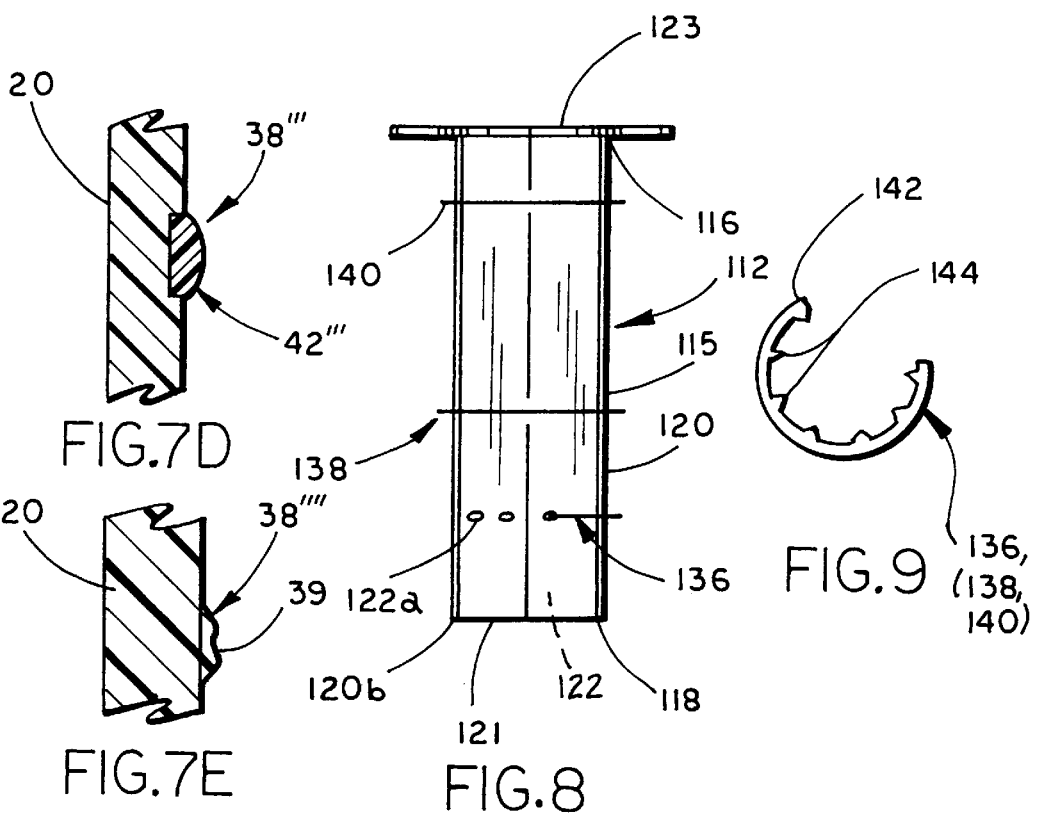
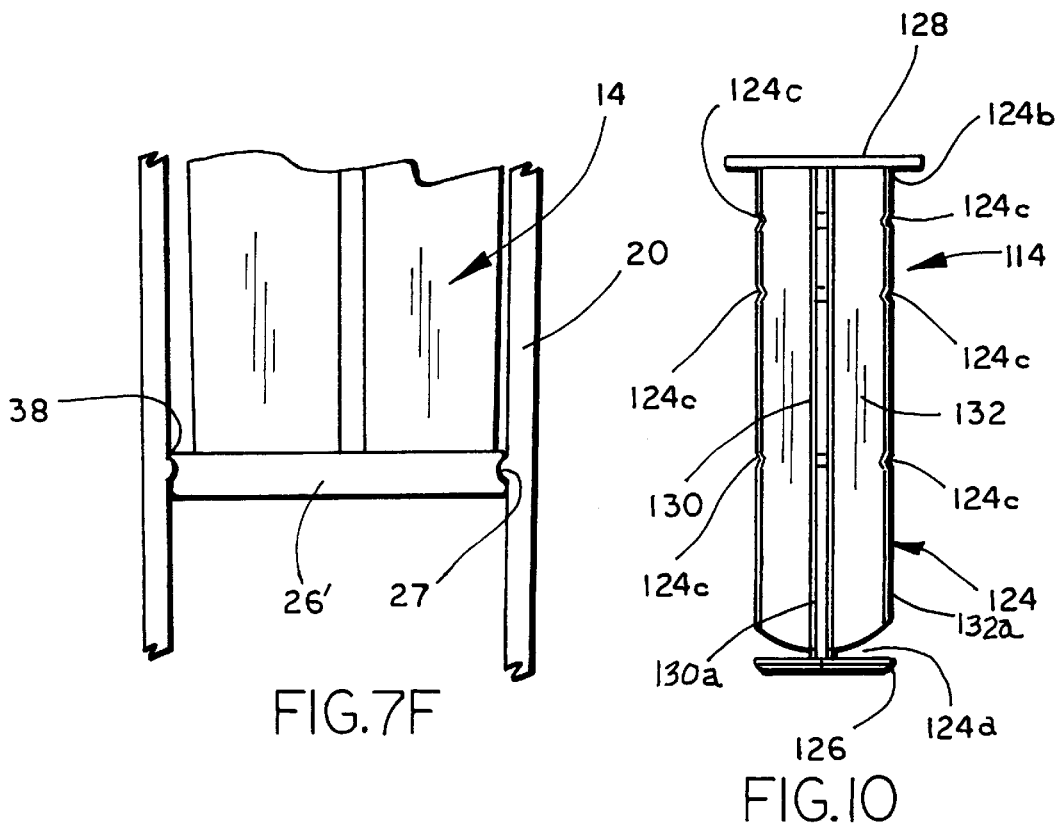

SOIL SAMPLING MEASURING DEVICE

TECHNICAL FIELD AND BACKGROUND OF THE INVENTION

The present invention relates to a soil sampling device and, more particularly, to a self contained volatile soil sampling device for measuring a sample of soil in the field.

Generally there are two approved ways for collecting soil samples for volatile soil analysis: A sealed soil sampling device method and methanol preservation method. Off-site testing requires a soil sample to be preserved so that accurate testing can be later accomplished at an off-site laboratory. Typically, a sample of soil is taken and enclosed in a container. The container is sealed to retain the volatile compounds in the soil and then transported to the off-site laboratory where the soil sample can be tested.

In contrast, methanol preservation requires a sample of soil to be weighed and placed into a sample jar. A controlled amount of pure methanol is measured in a graduated cylinder and poured into the sample jar. The sample jar is then shaken for two minutes and prepared for shipping to an off-site laboratory. In this manner, the volatile compounds in the soil are preserved by the methanol. Typically, a second sample jar is filled with another sample of the soil which is forwarded along with the first sample to the off-site laboratory and is used to determine the dry weight of the soil. Consequently, the on-site preservation procedure analysis requires weighing the soil and measuring methanol which results in a relatively labor intensive process.

More recently, methanol ampoules have been produced which provide a fixed volume of the methanol, thus eliminating the need to measure out the methanol. However, heretofore, such simple measuring devices for soil are not available. Consequently, there is a need for a simple soil sampling device which permits accurate measurement of a soil sample without the need for a weighing device and, further, provides a simple quick method of measuring with fewer steps and fewer components than heretofore known.

SUMMARY OF THE INVENTION

Accordingly, the present invention provides a new and unique soil sampling device, which is especially suitable for the methanol preservation method of collecting samples of soil for testing the volatile organic compounds (VOCs) in the soil. The soil sampling device includes a tactile indication of the volume of soil collected in the sampling device, which volume must be determined in order to use the methanol preservation method.

According to one aspect of the invention, a soil sampling device includes a body and a plunger. The body includes a first end and a second end and a cylindrical wall that extends between the first and second ends. The second end is open and defines an insertion end for inserting into soil. The plunger extends through the first end of the body and frictionally engages the inner surface of the cylindrical wall. The cylindrical wall or the plunger includes at least one indicator corresponding to a selected volume of the body. The indicator provides a change in resistance between the body and the plunger so that a person pushing or pulling on the plunger can detect the change in resistance between the plunger and the body thereby providing a tactile indication to the person that the plunger has reached a desired position in the body.

In preferred aspects of the invention, the indicator may comprise a raised or projecting rib or a groove or a plurality of spaced discrete raised or recessed portions.

In other aspects, the indicators are provided on the cylindrical wall of the body. Optionally, the indicator extends around at least a portion of the inner circumference of the cylindrical wall.

According to another aspect of the invention, a soil sampling device includes a body and a plunger. The body includes a first end and a second end and a cylindrical wall, which extends between the first end and the second end. The second end of the cylindrical wall is open and defines a mouth, with the mouth having a width equal to the inner diameter of the cylindrical wall. The plunger extends through the first end of the body and frictionally engages the inner surface of the cylindrical wall.

In other aspects, the cylindrical wall includes at least one circumferentially extending indicator. The plunger frictionally engages the inner surface of the cylindrical wall with a first friction force and frictionally engages the indicator with a second friction force whereby a person pushing or pulling on the plunger can detect the change in resistance between the plunger and the inner surface of the cylindrical wall and the plunger and the indicator thereby providing a tactile indication that the plunger has reached the indicator.

In preferred aspects, the indicator comprises a groove or projecting rib, where the groove provides a lower resistance between the plunger and the cylindrical wall, and the rib provides an increased resistance between the plunger and the cylindrical wall. In further aspects, the indicator may have a higher coefficient of friction than the coefficient of friction of the inner surface of the cylindrical wall so that the user of the soil sampling device will detect an increase in resistance between the plunger and the cylindrical wall when the plunger is positioned at an indicator.

In other aspects of the invention, a method of sampling a soil includes providing a soil sampling device which comprises a body and a plunger with a piston. The body includes a first end and a second end and a cylindrical wall extending between the first and second ends. The second end is open and defines a mouth for inserting into soil. The plunger extends through the first end of the body and frictionally engages the inner surface of the cylindrical wall. The plunger is first extended into the cylindrical body, and then the soil sampling device is inserted into the soil while the plunger is withdrawn into the body of the soil sampling device. Upon detecting a change in resistance between the plunger and the body, the plunger is released to hold the position of the plunger so that a desired volume of soil is collected in the body.

As will be understood, the soil sampling device of the present invention provides numerous advantages over prior known soil sampling devices. The soil sampling device provides a multiple-use device which consists of two parts, the soil sampling device body and plunger with a piston. The soil sampling device is simple to use and overcomes the handling problems of prior known soil sampling devices and provides a simple device for measuring soil. Furthermore, when the piston is retracted into the sampling device body, a person pulling on the plunger can detect when the piston has reached selected positions in the sampling device body which correspond to desired weights of the soil sample. These and other objects, advantages, purposes, and features of the invention will become more apparent from the study of the following description taken in conjunction with the drawings.

BRIEF DESCRIPTION OF THE DRAWINGS

FIG. 7D is a similar cross-sectional view to FIG. 7A illustrating a fourth embodiment of a volume indicator of the soil sampling device;

FIG. 7E is a similar cross-sectional view to FIG. 7A illustrating a fifth embodiment of a volume indicator;

FIG. 7F is an enlarged cross-sectional view similar to the cross-section taken along line VII—VII of FIG. 1 when the piston is aligned with an indicator;

FIG. 8 is a second embodiment of a barrel of the soil sampling device of the present invention;

FIG. 9 is a plan view of a sixth embodiment of the volume indicator of the soil sampling device; and FIG. 10 is a second embodiment of a plunger of the soil sampling device of the present invention.

DESCRIPTION OF THE PREFERRED EMBODIMENTS

Figure 1:
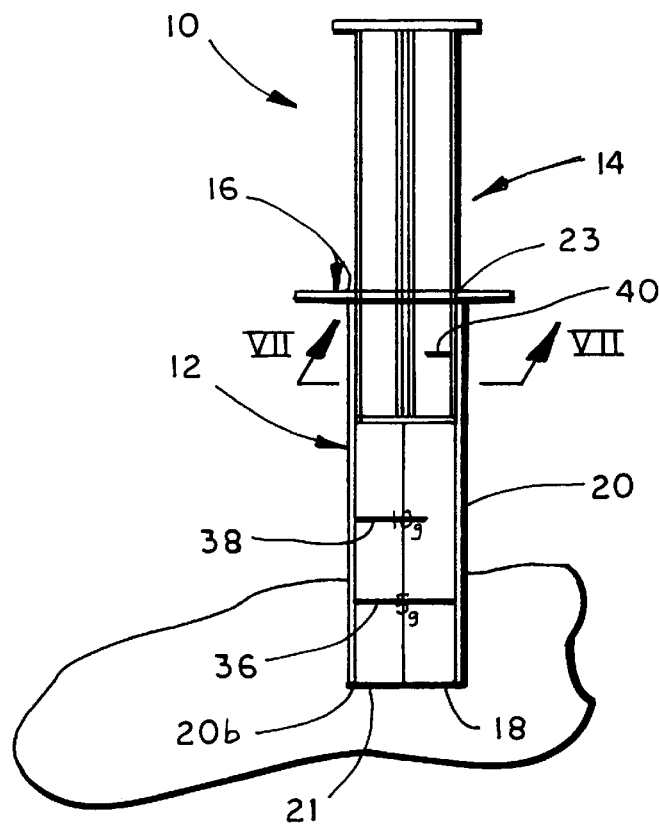
FIG. 1 is a side view of a soil sampling device of the present invention.

Referring to FIG. 1, the numeral 10 generally designates a soil sampling device of the present invention. Soil sampling device 10 includes a barrel 12 and a plunger 14 which is positioned in the barrel for measuring the soil collected in barrel 12 and for expelling the collected soil from the barrel for testing. Barrel 12 and plunger 14 are preferably made from a plastic material, such as a polymer. As will be more fully described below, barrel 12 is formed or arranged so that when plunger 14 is extended through barrel 12, the person applying a force to plunger 14 will be able to detect when the plunger 14 reaches selected locations along the barrel which correspond to desired volumes of the soil for measuring the weight of the soil.

Figure 2:
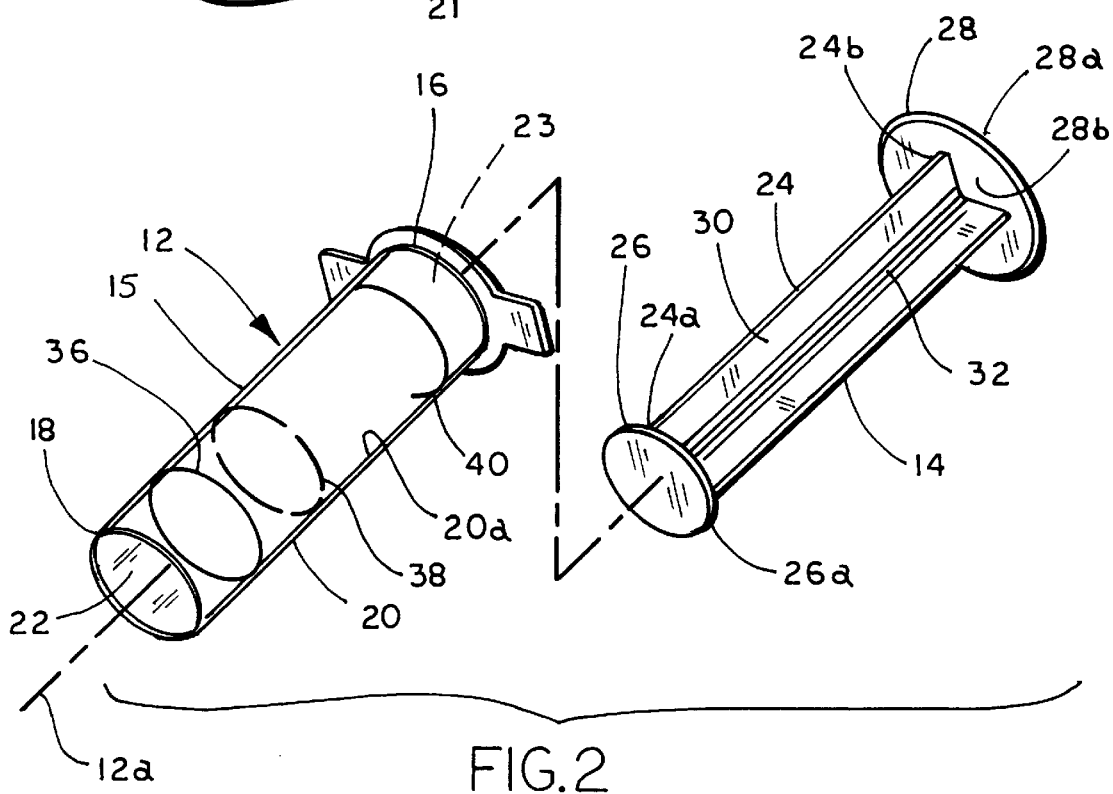
FIG. 2 is an exploded perspective view of the soil sampling device of FIG. 1.
Figure 3:
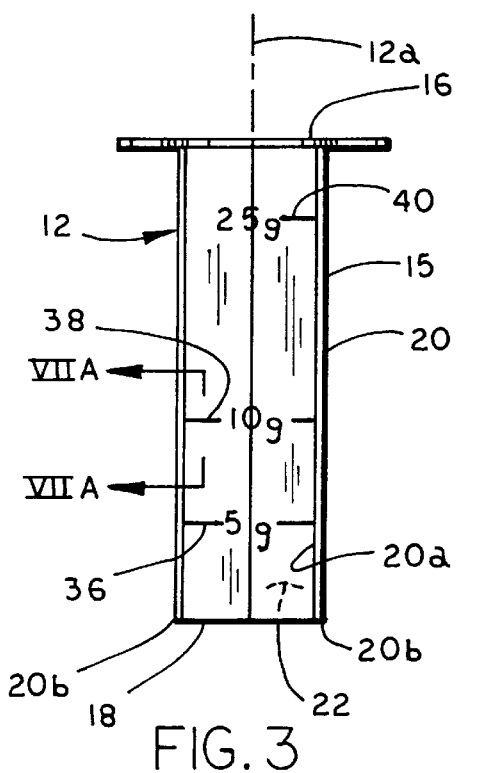
FIG. 3 is a side view of a barrel of the soil sampling device of FIG. 1.
Figure 4:
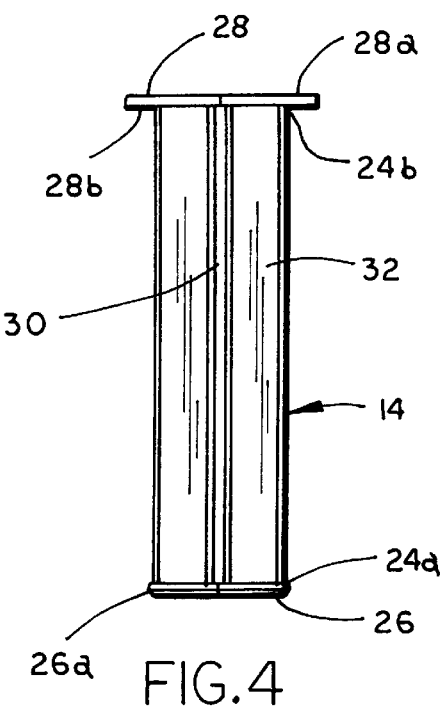
FIG. 4 is a plunger of the soil sampling device of FIG. 1.
Figure 5:
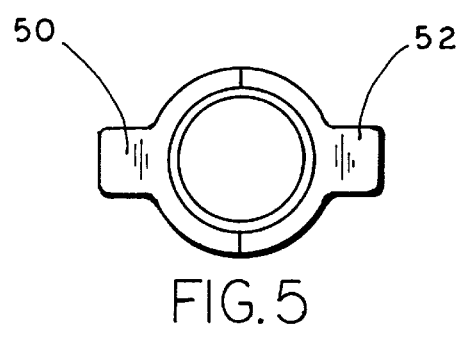
FIG. 5 is a top plan view of the barrel of FIG. 3.
Figure 6:
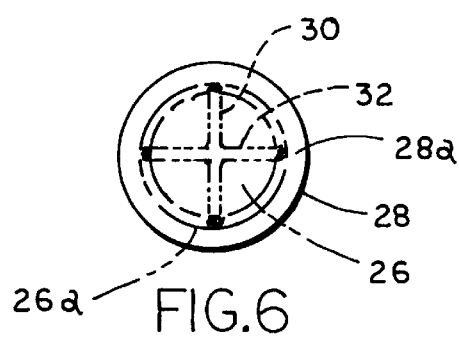
FIG. 6 is a top plan view of the plunger of FIG. 4.

As best seen in FIG. 2, barrel 12 comprises a body 15 which includes a first end 16 and a second end 18 and a cylindrical wall 20 which extends between first end and second end 16 and 18. Second end 18 is open and defines a mouth 21 for inserting into the soil. Preferably, mouth 21 has a width equal to the inner diameter of cylindrical wall 20 such that mouth 21 extends between the terminal ends 20b of cylindrical wall 20. First end 16 of barrel 12 includes a pair of projecting arms 50 and 52 to ease insertion of second end 18 into the soil.

Plunger 14 extends through an opening 23 provided in first end 16 for measuring a sample of soil collected in barrel 12 after soil sampling device has been inserted into the soil, as will be more fully described in reference to the method discussed below. Plunger 14 includes a shaft 24 with a piston 26 formed or attached on one end 24a of shaft 24 and a handle 28 formed or attached on an opposed end 24b of shaft 24. Shaft 24 optionally includes a cross-shaped body formed from two intersecting planar members 30 and 32. Planar members 30 and 32 preferably extend from handle 28 to piston 26 and substantially extend across piston 26 thereby providing stiffness to piston 26. However, it should be understood that planar members 30 and 32 may taper down to a reduce width to vary the stiffness of piston 26.

As best seen in FIGS. 1 and 2, handle 28 is generally planar and projects outwardly from planar members 30 and 32 to provide a pressing surface 28a on one side and a pulling surface 28b on an opposed side of handle 28. Piston 26 is generally dish-shaped and includes an outer perimeter 26a for engaging an inner surface 20a of cylindrical wall 20. Optionally, piston 26 may include a sealing member positioned on outer perimeter 26a for frictionally engaging inner surface 20a. In addition, piston 26 may optionally include a pair of sealing members for engaging inner surface 20a, as would be understood by those skilled in the art.

Referring again to FIG. 2, cylindrical wall 20 includes a plurality of volume indicators 36, 38, and 40. Volume indicators 36, 38, and 40 are positioned and spaced at selected positions along the longitudinal axis 12a of barrel 12. Volume indicators 36, 38, and 40 provide a physical indication of the selected volumes in barrel 12, which correspond with selected weights of a typical soil sample. As will be more filly described below, volume indicators 36, 38, and 40 provide a tactile indication to the user of soil sampling device 10 of the location of the plunger within the barrel so that the volume of the soil collected in barrel 12 can be determined without reference to a visual scale on the side of the barrel.

Figure 7A:
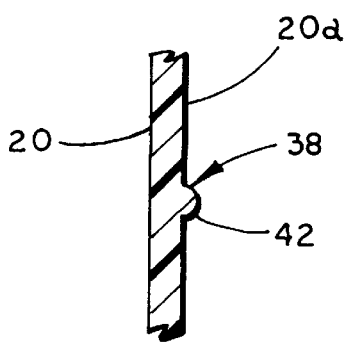
FIG. 7A is a cross-sectional view taken along line VII-A—VII-A of FIG. 3 illustrating a first embodiment of a volume indicator of the soil sampling device.

Preferably, volume indicators 36, 38, and 40 provide a change in resistance between the inner surface 20a of cylindrical wall 20 and piston 26. Referring to FIG. 7A, volume indicator 38 (36, or 40) may comprise a projecting member or rib 42. In the illustrated embodiment, projecting rib 42 comprises an arcuate rib, but it should be understood that the rib may have other cross-sections that increase the resistance between piston 26 and cylindrical wall 20. By increasing the resistance between the piston 26 and the cylindrical wall, a person pulling or pushing on handle 28 will be able to detect when piston 26 is aligned with the respective volume indicator 36, 38, or 40. Consequently, a person using the soil sampling device 10 may detect when a fixed volume and corresponding fixed weight of soil has been received into the barrel 12. In addition, volume indicators 36, 38, or 40 may comprise an annular indicator that extends around the full inner circumference of cylindrical wall 20. Alternately, volume indicators 36, 38, or 40 may be formed from discrete segmented portions which are spaced and aligned in a plane which extends around circumference of the inner surface of cylindrical wall 20. Furthermore, volume indicators 36, 38, and 40 may comprise arcuate indicators that extend around a portion of the circumference of the inner surface of cylindrical wall 20. Other variations include the volume indicators comprising a plurality of knobs which are generally aligned along a line defined in a plane which extends around the inner surface 20a of the cylindrical wall 20.

Figure 7B:
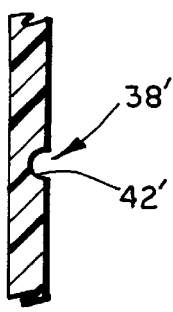
FIG. 7B is a similar cross-sectional view to FIG. 7A illustrating a second embodiment of a volume indicator of the soil sampling device.

Alternately, as seen in FIG. 7B, a second embodiment of volume indicator 38' may comprise a recess or groove 42', which provides a reduced friction force between cylindrical wall 20 and piston 26. In a similar manner to volume indicator 38, volume indicator 38' may comprise an annular indicator or an arcuate indicator or the like.

Figure 7C:
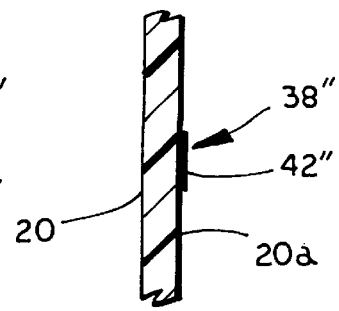
FIG. 7C is a similar cross-sectional view to FIG. 7A illustrating a third embodiment of a volume indicator of the soil sampling device.

Referring to FIG. 7C, a third embodiment of volume indicator 38" is illustrated. Volume indicator 38" comprises a surface 42″ with an increase coefficient of friction to thereby provide a tactile indication to the use of the location of piston 26 within barrel 12. For example, inner surface 20*a* of cylindrical wall 20 may be treated or may be formed with an irregular surface to thereby form surface 42″. Moreover, referring to FIG. 7D, cylindrical wall 20 may be provided with an insert 42‴ which is positioned in a groove and held in place, by for example friction or an adhesive or the like. Optionally, insert 42‴ may be insert or injection molded with barrel 12. Insert 42‴, in a similar manner to surface 42″, has a different coefficient of friction than inner surface 20*a* of cylindrical wall 20.

In yet another embodiment illustrated in FIG. 7E, cylindrical wall 20 may include a projecting indicator 38″″ with a groove 39 formed therein. Groove 39 provides a seat for the piston. Thus, when the plunger is pulled or withdrawn into the body of the sampling device, the piston will exhibit an increased resistance between the piston and projecting indicator 38″″. However, as the user continues to pull, the piston will exhibit a slight decrease in friction when the piston engages groove 39 thus providing a more accurate indication that the piston is positioned in the desired location within the body of the sampling device. Alternately, as best seen in FIG. 7F, piston 26′ optionally includes an annular groove 27 which provides a similar decrease in resistance between piston 26′ and indicator 38 when indicator 38 is seated in groove 27. In this manner, a user can initially detect the increase resistance between piston 26′ and indicator 38 and then detect a subsequent reduction in the friction between the piston 26′ and indicator 38 followed by another increase in resistance, thus, providing the user with a more accurate means of locating the piston at a desired position along the longitudinal axis the body of the sampling device.

Referring to FIG. 8, a second embodiment of barrel 112 is illustrated. Barrel 112 comprises a body 115 which includes a first end 116 and a second end 118 and a cylindrical wall 120 which extends between first and second ends 116 and 118. Second end 118 is open and defines a mouth 121 for inserting into the soil. Preferably, mouth 121 has a width equal to the inner diameter of cylindrical wall 120 such that mouth 121 extends between the terminal ends 120*b* of cylindrical wall 120.

Plunger 14 extends through an opening 123 provided in first end 116 of body 115 for measuring a sample of soil collected in barrel 112 after the soil sampling device has been inserted into the soil in a similar manner described in reference to the first embodiment of the soil sampling device. As best seen in FIG. 8, cylindrical wall 120 includes a plurality of spaced apart apertures 122*a*. In the illustrated embodiment apertures 122*a* are spaced apart and aligned in a plane that extends around at least a portion of the circumference of cylindrical wall 120. Similar to the previous embodiment, barrel 112 includes a plurality of volume indicators 136, 138, and 140. Referring to FIG. 9, indicator 136 (138 and 140) comprises an arcuate member 142 with a plurality of inwardly projecting members 144 which are spaced and aligned to correspond to apertures 122*a* of barrel 112. Indicators 136, 138, and 140 are mounted on cylindrical wall 120 by a snap fit, with each of the projecting members 144 extending through the respective apertures so that the projecting members project into passageway 122 of barrel 112 to provide an increase resistance between piston 26 and barrel 112. It should be understood from the foregoing the number of projecting members can be increased or decreased as desired.

In yet another embodiment, plunger 114 is adapted to provide a tactile indication of the location of its piston 126 in barrel 12 or 112. Similar to the first embodiment, plunger 114 includes a shaft 124 with a piston 126 formed or provided on a first end 124*a* of shaft 124 and a handle 128 formed or provided on a second opposed end 124*b* of shaft 124. In this embodiment, shaft 124 of plunger 114 is sized to frictionally engage opening 23 or 123 of barrel 12 or 112. Furthermore, barrel 12 or 112 may comprise a continuos smooth walled barrel with the tactile indication being provided only by the change of friction between plunger 114 and opening 23 or 123, as will be more fully described below.

As best seen in FIG. 10, shaft 124 is formed or is provided with a plurality of grooves 124*c* at its outer perimeter. Grooves 124*c* are spaced apart along shaft 124 and positioned to correspond to a desired volume on barrel 12 or 112. In the illustrated embodiment, shaft 124 is formed from intersecting planar members 130 and 132 in which case, grooves 124*c* are formed or provided on the distal edges 130*a* and 132*a* of members 130 and 132 which define the outer perimeter of shaft 124. In this embodiment, planar members 130 and 132 are tapered at end 124*a* to reduce the stiffness of piston 126.

Thus, when plunger 114 is inserted through opening 23 or 123 of barrel 12 or 112 and pushed into barrel 12 or 112 a person using the soil sampling device will be able to detect the change in resistance between plunger 114 and opening 23 or 123 to determine when piston 126 is located in a desired position in barrel 12 or 112. It should be understood that plunger 114 may alternately include projecting members which provide an increased friction between plunger 114 and opening 23 or 123.

From the foregoing, it can be appreciated that an improved method of soil sampling is disclosed. Plunger 14 or 114 is pushed into barrel 12 or 112 so that piston 26 or 126 is positioned at open end 18 or 118 of barrel 12 or 112. After fully extending plunger 14 or 114 into barrel 12 or 112, a force is applied to projecting arms 50 and 52 of barrel 12. Upon applying a force to arms 50, 52, cylindrical wall 20 or 120 extends into the soil with the soil entering chamber 22 or 122 of barrel 12 or 112 through open end 18 or 118. As the soil enters passageway 22 or 122, plunger 14 or 114 is manually retracted until the user detects a change in resistance between either the plunger 114 and the opening of the barrel or between piston 26 and cylindrical wall 20 or 120. In this manner, the person using soil sampling device 10 may tactiley detect when the soil sampler is filled to a desired volume with the soil and thereby measure a desired weight of the soil.

While several forms of the invention have been shown and described, other forms will now become apparent to those skilled in the art. For instance, barrel 12 or plunger 14 may be formed from other materials including a metal material. Furthermore, inner surface 20*a* may be ramped on either side of the volume indicator to provide a signal when the piston is approaching a volume indicator. The embodiment of the invention shown in the drawings is not intended to limit the scope of the invention which is defined by the claims which follow.

We claim:

1. A soil sampling device comprising:
   a body having a first end and a second end and a cylindrical wall extending between said first end and said second end, said second end being open and defining an insertion end for inserting into soil; and
   a plunger extending through said first end, said cylindrical wall having an inner surface, said plunger frictionally engaging said inner surface to substantially seal against said inner surface, and one of said plunger and said inner surface including at least one indicator corresponding to a selected volume of said cylindrical body, said indicator providing a change in resistance between said body and said plunger whereby a person pushing or pulling on said plunger can detect the change in resistance thereby providing a tactile indication that said plunger has reached said indicator, said indicator comprising a groove formed on one of said plunger and said cylindrical wall.

2. A soil sampling device according to claim 1, wherein said indicator comprises an annular indicator.

3. A soil sampling device according to claim 1, wherein said cylindrical wall includes said at least one indicator, said indicator comprising an arcuate indicator extending around at least a portion of an inner circumference of said cylindrical wall.

4. A soil sampling device according to claim 1, wherein said plunger includes at least one sealing member.

5. A soil sampling device according to claim 1, wherein said cylindrical wall includes a terminal end, said open end extending between said terminal end of said cylindrical wall.

6. A soil sampling device according to claim 1, wherein said cylindrical wall includes an inner diameter, said open end having an opening width equal to said inner diameter of said cylindrical wall.

7. A soil sampling device comprising:
a body having a first end and a second end and a cylindrical wall extending between said first end and said second end, said second end being open and defining an insertion end for inserting into soil; and
a plunger extending through said first end, said cylindrical wall having an inner surface, said plunger frictionally engaging said inner surface to substantially seal against said inner surface, and one of said plunger and said inner surface including at least one indicator corresponding to a selected volume of said cylindrical body, said indicator providing a change in resistance between said body and said plunger whereby a person pushing or pulling on said plunger can detect the change in resistance thereby providing a tactile indication that said plunger has reached said indicator, said indicator comprising a rib formed on said cylindrical wall.

8. A soil sampling device comprising:
a body having a first end and a second end and a cylindrical wall extending between said first end and said second end, said second end being open and defining an insertion end for inserting into soil; and
a plunger extending through said first end, said cylindrical wall having an inner surface, said plunger frictionally engaging said inner surface to substantially seal against said inner surface, and one of said plunger and said inner surface including at least one indicator corresponding to a selected volume of said cylindrical body, said indicator providing a change in resistance between said body and said plunger whereby a person pushing or pulling on said plunger can detect the change in resistance thereby providing a tactile indication that said plunger has reached said indicator, said cylindrical wall including a plurality of said indicators.

9. A soil sampling device according to claim 8, wherein said plurality of indicators comprise a plurality of one of a rib and a groove.

10. A soil sampling device comprising:
a body having a first end and a second end and a cylindrical wall extending between said first end and said second end, said second end being open and defining an insertion end for inserting into soil; and
a plunger extending through said first end, said cylindrical wall having an inner surface, said plunger frictionally engaging said inner surface to substantially seal against said inner surface, and one of said plunger and said inner surface including at least one indicator corresponding to a selected volume of said cylindrical body, said indicator providing a change in resistance between said body and said plunger whereby a person pushing or pulling on said plunger can detect the change in resistance thereby providing a tactile indication that said plunger has reached said indicator, said inner surface of said cylindrical wall including a first coefficient of friction, said indicator comprising a surface having a second coefficient of friction, wherein said first coefficient of friction is different than said second coefficient of friction.

11. A soil sampling device comprising:
a body having a first end and a second end and a cylindrical wall extending between said first end and said second end, said cylindrical wall having an inner surface and an inner diameter, said second end being open and defining a mouth, said mouth having a width equal to said inner diameter of said cylindrical wall, said inner surface having at least one circumferentially extending indicator; and
a plunger extending through said first end of said body, and said plunger including a handle and frictionally engaging said inner surface of said cylindrical wall with a generally constant friction force, said plunger frictionally engaging said inner surface of said cylindrical wall with a first resistance, and said plunger frictionally engaging said indicator with a second resistance whereby a person pushing on said plunger can detect the change in resistance between said plunger and cylindrical wall and said plunger and said indicator thereby providing a tactile indication that said plunger has reached said indicator.

12. A soil sampling device according to claim 11, wherein said indicator comprises one of a groove and a rib.

13. A soil sampling device according to claim 12, wherein said indicator comprises an annular indicator extending 360 degrees around an inner circumference of said cylindrical wall.

14. A soil sampling device according to claim 12, wherein said inner surface of said cylindrical wall has a first coefficient of friction, and said indicator has a second coefficient of friction wherein said first coefficient of friction is different than said second coefficient of friction.

15. A method of soil sampling comprising the steps of:
providing a soil sampling device comprising a body having a first end and a second end and a cylindrical wall extending between said first and second ends, said second end being open and defining a mouth, the soil sampling device further including a plunger having a piston, said plunger extending through said first end, one of the plunger and the cylindrical wall having at least one indicator, said indicator providing a tactile indication of when the piston reaches a desired location in said body:
extending said plunger into said cylindrical body:
inserting said soil sampling device into a sample of soil;
withdrawing said plunger into said body of said soil sampling device in a direction from said second end to said first end;

detecting a change of resistance between the body and the plunger; and upon detecting a change of resistance releasing the plunger to hold the piston of the plunger at least in close proximity to the indicator, said detecting including detecting an increase in resistance between the plunger and the body.

16. A method of soil sampling comprising the steps of:

providing a soil sampling device comprising a body having a first end and a second end and a cylindrical wall extending between said first and second ends, said second end being open and defining a mouth, the soil sampling device further including a plunger having a piston, said plunger extending through said first end, one of the plunger and the cylindrical wall having at least one indicator, said indicator providing a tactile indication of when the piston reaches a desired location in said body:

extending said plunger into said cylindrical body;

inserting said soil sampling device into a sample of soil;

withdrawing said plunger into said body of said soil sampling device in a direction from said second end to said first end;

detecting a change of resistance between the said body and the plunger; and upon detecting a change of resistance releasing the plunger to hold the piston of the plunger at least in close proximity to the indicator, said detecting including detecting an increase in resistance between the piston and the cylindrical wall.

17. A method of soil sampling comprising the steps of:

providing a soil sampling device comprising a body having a first end and a second end and a cylindrical wall extending between said first and second ends, said second end being open and defining a mouth, the soil sampling device further including a plunger having a piston, said plunger extending through said first end, one of the plunger and the cylindrical wall having at least one indicator, said indicator providing a tactile indication of when the piston reaches a desired location in said body;

extending said plunger into said cylindrical body;

inserting said soil sampling device into a sample of soil;

withdrawing said plunger into said body of said soil sampling device in a direction from said second end to said first end;

detecting a change of resistance between the said body and the plunger; and upon detecting a change of resistance releasing the plunger to hold the piston of the plunger at least in close proximity to the indicator, said detecting including detecting a decrease in resistance between said body and said plunger.

* * * * *